United States Patent [19]

Pesa et al.

[11] 4,301,090
[45] Nov. 17, 1981

[54] CARBONYLATION OF OLEFINICALLY UNSATURATED COMPOUNDS

[75] Inventors: Frederick A. Pesa, Aurora; Thomas A. Haase, Twinsburg, both of Ohio

[73] Assignee: Standard Oil Company, Cleveland, Ohio

[21] Appl. No.: 66,146

[22] Filed: Aug. 13, 1979

Related U.S. Application Data

[62] Division of Ser. No. 955,861, Oct. 30, 1978, Pat. No. 4,235,744.

[51] Int. Cl.$^3$ .............. C07C 120/00; C07C 121/417; C07C 121/16
[52] U.S. Cl. .................... 260/465.4; 260/343.6; 260/465.1; 260/465.6; 560/179; 560/187; 560/233; 564/132; 568/429; 568/455; 568/594; 568/600
[58] Field of Search ............. 260/465.1, 465.4, 465.6, 260/561 B, 561 R; 560/233, 187, 179; 568/594, 600, 429, 455; 564/132

[56] References Cited

U.S. PATENT DOCUMENTS

| | | | |
|---|---|---|---|
| 3,010,994 | 11/1961 | Iwanaga et al | 260/465.1 X |
| 3,278,612 | 10/1966 | Greene | 260/632 |
| 3,507,891 | 4/1970 | Hearne et al. | 560/233 X |
| 3,546,269 | 12/1970 | Wakamatsu et al. | 260/465.6 |
| 3,594,425 | 7/1971 | Brader, Jr. et al. | 260/604 HF |
| 3,856,832 | 12/1974 | Keblys | 560/233 X |
| 3,857,895 | 12/1974 | Booth | 260/604 HF |
| 3,931,332 | 1/1976 | Wilkes | 260/604 HF |
| 3,968,128 | 7/1976 | McVicker | 260/604 HF X |
| 4,041,057 | 8/1977 | Fanning | 560/233 X |
| 4,045,492 | 8/1977 | Kniese et al. | 260/604 HF |
| 4,060,543 | 11/1977 | Weitz et al. | 260/465.4 |
| 4,141,915 | 2/1979 | El-Chahawi et al. | 260/465.4 X |
| 4,201,868 | 5/1980 | Slinkard | 568/594 X |

OTHER PUBLICATIONS

Falbe, "Carbon Monoxide in Organic Synthesis", 1970, pp. 8, 9 and 49.

*Primary Examiner*—Joseph Paul Brust
*Attorney, Agent, or Firm*—Larry W. Evans; Joseph G. Curatolo; Herbert D. Knudsen

[57] ABSTRACT

Oxygenated organic compounds, e.g. esters, aldehydes, and amides, are prepared by reacting an olefinically unsaturated compound with carbon monoxide and a compound containing a replaceable hydrogen atom in the presence of a catalyst comprising cobalt carbonyl and a polyamine promoter ligand. These reactions are carried out under relatively mild conditions of temperature and pressure.

12 Claims, No Drawings

CARBONYLATION OF OLEFINICALLY UNSATURATED COMPOUNDS

This is a division of application Ser. No. 955,861 filed Oct. 30, 1978, now U.S. Pat. No. 4,235,744, issued Nov. 25, 1980.

BACKGROUND OF THE INVENTION

The present invention relates to a novel process for producing oxygenated organic compounds.

There are several known methods for producing oxygenated organic compounds. The acid catalyzed ($H_2SO_4$, $HBF_4$, etc.) synthesis of carboxylic acids or esters by the reaction of an olefinic substrate with CO and water or alcohol has been known since 1931. (J. Falbe, "Carbon Monoxide in Organic Synthesis", Springer-Verlag, New York (1970)). Although this process was used on a commercial scale it does have serious limitations due to the reaction conditions and the isomeric composition of the products.

A more commercially important synthesis of carboxylic acid/esters is the direct carbonylation of olefinic substrates with CO and water/alcohol conducted in the presence of transition metals. In general, this carbonylation reaction, discovered by Repp in 1940 (I. Wender and P. Pino, "Organic Synthesis Via Metal Carbonyls", Volume 2, John Wiley, New York (1977)), involves the addition of carbon monoxide, carboxyl alkyl or amide group (Y—H where Y equals —OR or —NHR and R is an alkyl), and an olefin.

However, when an unsymmetrical olefin is used as the substrate at least two isomeric products are obtained. No general method has been developed for the control of the isomeric product composition.

The present invention overcomes some of these problems present in the prior art. For example, the inventive process results in higher conversions, higher yields and faster reaction rates than those disclosed in the prior art. Furthermore, the instant process allows one to obtain a high yield of a particular isomeric product composition. Thus, extremely high selectivities of particular oxygenated organic compounds can be obtained by the inventive process.

Finally, the prior art carbonylation reactions operate under extreme conditions of temperature and pressure. In general, temperatures in the range of 160° C. to 300° C. and pressures in the range of 1,500 to 5,000 psi are required. On the other hand, the present reaction may be carried out under relatively mild conditions of temperature and pressure. This further advantage can result in substantial cost savings in the production of oxygenated organic compounds.

SUMMARY OF THE INVENTION

It has now been discovered that oxygenated organic compounds can be produced by contacting an olefinically unsaturated compound with carbon monoxide and a compound containing a replaceable hydrogen atom in the presence of a catalyst comprising cobalt and/or ruthenium carbonyl and a polyamine promoter ligand.

In particular, the inventive process results in high yields of oxygenated organic compounds when operating at much lower temperatures and pressures than disclosed in the prior art. In addition, the instant process is very selective towards the branched-isomer.

Thus, the present invention provides a novel catalyst comprising a polyamine promoter ligand and at least one of cobalt and ruthenium carbonyl. Furthermore, the instant invention provides a novel process for the production of an oxygenated organic compound comprising contacting an olefinically unsaturated compound with carbon monoxide and a compound containing a replaceable hydrogen atom in the presence of the above catalyst. Finally, the present invention provides a novel process for the production of an oxygenated organic compound comprising contacting an olefinically unsaturated compound containing an alcohol moiety with carbon monoxide in the presence of the above catalyst.

Specifically, the carbonylation reaction of acrylonitrile, carbon monoxide, hydrogen gas, and methanol to yield methyl-α-cyanopropionate proceeds smoothly using a catalyst comprising cobalt carbonyl and a polyamine promoter ligand.

DETAILED DESCRIPTION

According to the present invention, it has been discovered that improved yields and selectivities of oxygenated organic compounds can be obtained by contacting an olefinically unsaturated compound with carbon monoxide and a compound containing a replaceable hydrogen atom over a catalyst comprising cobalt and/or ruthenium carbonyl and a polyamine promoter ligand. The overall reaction taking place in this process is represented by the following equation:

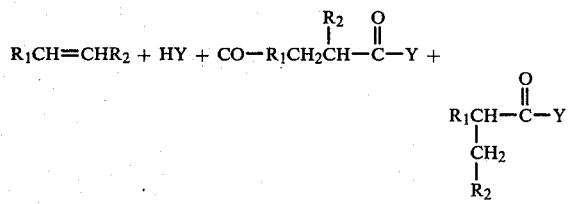

$R_1$, $R_2$ and Y are defined below.

Reactants

Olefinically unsaturated compounds which can be employed as reactants in the inventive process have the following structure:

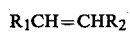

wherein $R_1$ and $R_2$ are each independently selected from:

(1) hydrogen (either $R_1$ or $R_2$ but not both);
(2) $C_{1-30}$ alkyl;
(3) —$(CH_2)_P$—CN, wherein P is 0–3; and
(4) —$(CH_2)_q$—$OR_3$, wherein q is 1–30 and $R_3$ is hydrogen or methyl.

Preferably, the olefinically unsaturated compounds comprise compounds wherein $R_1$ and $R_2$ are each independently selected from:

(1) hydrogen (either $R_1$ or $R_2$ but not both);
(2) $C_{1-10}$ alkyl;
(3) —$(CH_2)_P$—CN, wherein P is 0–2; and
(4) —$(CH_2)_q$—OH, wherein q is 1–10.

Most preferably, the olefinically unsaturated compounds comprise compounds wherein $R_1$ and $R_2$ are each independently selected from hydrogen (either $R_1$ or $R_2$ but not both), methyl and —$(CH_2)_P$—CN, wherein P is 0–1.

The second component in the inventive reaction system is a compound containing a replaceable hydrogen atom. This compound can be represented by the following formula:

H—Y wherein Y is selected from the group consisting of:
(1) $OR_5$ wherein $R_5$ is a $C_{1-30}$ alkyl;
(2)

wherein $R_6$ and $R_7$ are each independently selected from $C_{1-10}$ alkyls; and
(3) H.

Preferably Y is selected from the group consisting of:
(1) $OR_5$ wherein $R_5$ is a $C_{1-10}$ alkyl;
(2)

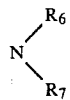

wherein $R_6$ and $R_7$ are each independently selected from $C_{1-4}$ alkyls; and
(3) H.

More preferably Y is selected from the group consisting of:
(1) $OR_5$ wherein $R_5$ is a $C_{1-4}$ alkyl; and
(2) H.

The second component is most preferably either methanol or hydrogen.

In the embodiment of the invention in which H-Y is an alcohol or amine, it is preferred to add hydrogen gas to the reaction system. Preferably the amount of hydrogen gas so added comprises less than 10% by volume of the total amount of the hydrogen gas and carbon monoxide gas in the reaction system. More preferably the hydrogen gas comprises 0.5% to 7.5% by volume of the hydrogen and carbon monoxide gas. The addition of hydrogen gas can increase both the yield and selectivity to desired products in this mode of the invention.

When $H_2$ is the compound containing a replaceable hydrogen atom then the reaction system will preferably contain 10% to 60% by volume hydrogen gas based on the total volume of the carbon monoxide and hydrogen gas. More preferably the reaction system will contain about 50% hydrogen gas.

One way to supply carbon monoxide and hydrogen gas into the reaction system is in the form of synthesis gas. The amount of hydrogen in the synthesis gas can be easily adjusted prior to insertion into the reactor.

The amount of carbon monoxide in the reaction system is not critical. Preferably the carbon monoxide is present in stoichiometric amounts and most preferably the carbon monoxide is present in amounts greatly in excess of stoichiometric amounts. If desired, a carrier gas which is inert to the reactants, products and catalyst can be included in the reaction system.

The molar ratio of the compound containing a replaceable hydrogen atom to the olefinically unsaturated compound can be 0.5-100.1 with a ratio of 1-10:1 being preferred. This ratio does not include the hydrogen gas which may be added to the reaction system when H-Y is an alcohol or amide.

In the embodiment of the invention in which the olefin reactant is an alcohol (i.e. wherein $R_1$ or $R_2$ is —$(CH_2)_q$—OH), it has been found that the terminal hydrogen atom on the alcohol group will itself serve as a replaceable hydrogen atom. As a result, the alcohol moiety of the olefin will react with the olefinic double bond of the olefin thereby producing a lactone. In this reaction system no H-Y component need be included since the olefin itself acts both as the olefin and the H—Y component. The reaction in this particular system is shown by the following equation:

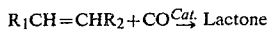

wherein at least one of $R_1$ and $R_2$ is an alcohol.

Process Conditions

Generally, in carrying out the inventive process, the olefinically unsaturated compound, carbon monoxide, and the compound containing a replaceable hydrogen atom are contacted with one another in the presence of the catalyst described below. The inventive reaction can be accomplished in the batch mode or continuously.

The reaction temperature is normally maintained between 50°–150° C. and most preferably at about 100° C. The reaction pressure is normally maintained at 100 to 2500 psi, preferably at 700 to 1000 psi. When the reaction is carried out in a batch mode, the reactants and catalysts are contacted with one another for a period of ten minutes through six hours, and preferably one half hour to four hours. A reaction time of less than ten minutes or more than six hours can be used if desired although better results will be obtained if the reaction time is maintained within this range. When the process is carried out on a continuous basis, the reaction catalyst contact time is normally 10 seconds to 10 minutes, preferably 100 seconds to 5 minutes.

Catalyst

The catalyst employed in the inventive processes comprises cobalt and/or ruthenium carbonyl and at least one polyamine promoter ligand in an inert organic solvent.

The inventive catalyst can be prepared by mixing the cobalt and/or ruthenium carbonyl with at least one polyamine promoter ligand and a solvent. The cobalt and/or ruthenium carbonyl and the polyamine promoter ligand may be added simultaneously or separately to the solvent. The exact relationship in the solvent between the cobalt and/or ruthenium carbonyl and the polyamine promoter ligand is not known.

Any solvent in which the catalyst is soluble may be used in the present invention. Preferably, the solvent is an alcohol, aromatic, ester, nitrile and/or dinitrile. The solvent is most preferably an alcohol or ester. In fact, the alcohol can be both the compound containing a replaceable hydrogen atom described above and the solvent. The preferred catalyst concentration in the solvent is normally between 0.1% to 5% by weight.

The cobalt and/or ruthenium carbonyl can be added to the solvent in any form from which cobalt and/or ruthenium carbonyl could be formed. For example, it is well known in the art that carbonyls can be formed from naphthalates and nitrates and thus suitable naphthanates and nitrates can be added to the solvent to form the carbonyl compound in situ. Preferably the catalyst contains cobalt carbonyl.

The polyamine promoter ligand has the following structure:

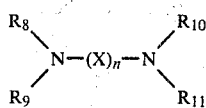

wherein X is selected from the group consisting:
(1) —$CH_2$—
(2) unsubstituted 6 member hydrocarbon rings; and
(3) substituted 6 member hydrocarbon rings substituted with 1 to 4 methyl groups; and wherein n is 0 to 10, with the proviso that when n is 0, $R_8$ is bonded to $R_{10}$ and $R_9$ is bonded to $R_{11}$ to form a cyclic structure in which the carbon framework of the heterocycle is unsaturated; and wherein $R_8$, $R_9$, $R_{10}$ and $R_{11}$ are each independently selected from the group consisting of:
(1) $C_{1-10}$ alkyls;
(2) unsubstituted 5 or 6 member hydrocarbon rings;
(3) substituted 5 or 6 member hydrocarbon rings substituted with 1 to 5 methyl groups;
(4) $C_{1-10}$ amides; and
(5) hydrogen.

Preferably X is $CH_2$, n is 3 to 5, and $R_8$, $R_9$, $R_{10}$ and $R_{11}$ are each independently selected from the group consisting of $C_{1-4}$ alkyls.

In general, the polyamine promoter ligand to cobalt and/or ruthenium carbonyl molar ratio is 0.5–4:1 and preferably about 2:1. This ratio will vary depending on the polyamine promoter ligand chosen. An increase in the ligand/transition metal ratio generally decreases the conversion but increases the selectivity for the iso-isomer.

Recovery

The reaction product obtained upon completion of the reaction is normally in the form of a liquid and composed primarily of unreacted reactants, catalyst and oxygenated organic compounds. This reaction product can be subjected to suitable known separation techniques, i.e. solvent extraction and fractional distillation, to yield the desired end products.

A particularly good method for separating the catalyst from the products obtained in the present process is by the use of conjugate phase extraction. In this separation scheme, the reaction effluent is treated with a $C_5$ to $C_8$ hydrocarbon which is miscible with the reaction solvent but which is a very poor solvent for the catalyst. Examples of such hydrocarbons are pentane, hexane and octane. Enough of this hydrocarbon is added to the reactor effluent to separate almost all of the catalyst into one phase and a significant amount of products into the other phase. Generally, this is between 1 to 4 volumes of hydrocarbon per volume of reactor effluent.

It is desirable to exclude oxygen from this separation system so that catalyst decomposition will not occur. It is also desirable to minimize the amounts of unreacted substrates in the reactor effluent prior to treatment with the hydrocarbon. This can be accomplished by simple distillation or vacuum stripping.

The catalyst containing hydrocarbon phase can be diluted and recycled back to the reactor. The product phase is then subjected to known separation techniques such as distillation or extraction.

The oxygenated organic compounds produced by this process are useful as precursors to polymers. The esters are also useful in perfumes, flavorings and pharmaceuticals. The aldehydes are useful as plasticizers and as intermediates for alcohols.

SPECIFIC EMBODIMENTS

In order to more thoroughly illustrate the present invention, the following working examples are presented. In these examples, the following definitions are used:

$$\% \text{ Conv} = \frac{\text{moles carbon in reactant converted to product}}{\text{moles carbon in reactant fed}} \times 100$$

$$\% \text{ Yield} = \frac{\text{moles carbon of olefinically unsaturated compound converted to product}}{\text{moles carbon of olefinically unsaturated compound fed}} \times 100$$

The results have all been adjusted to a 100% carbon balance.

In general, the experimental method consists of placing a pre-weighed solution of olefinically unsaturated compound, promoter ligand, compound containing a replaceable hydrogen atom and solvent into a glasslined autoclave. Next, cobalt and/or ruthenium carbonyl is added and the autoclave sealed.

The autoclave is flushed two times with synthesis gas and then charged with the synthesis gas to the desired pressure. The temperature is then increased and the reaction proceeds for 1 to 4 hours. Occasionally, samples are withdrawn during the course of the reaction through the vent tube and subjected to gas chromatography analysis. After the runs, the glasslined autoclave is brought to room temperature by cooling with cold water, depressurized and opened for product analysis.

The results of the experiments are shown in Table I. A glossery of terms follows Table I and specifies the meanings of the abbreviations used in Table I.

EXAMPLE 1

13.5 grams of acrylonitrile, 0.32 grams of ethylenediamine and 100 milliliters of methanol were placed in a glasslined autoclave. Next, 1.37 grams of $Co_2(CO)_8$ were added and the autoclave sealed.

The autoclave was charged with synthesis gas containing 5% $H_2$ until a pressure of 800 psi was reached. The temperature was set at 100° C. and the reaction proceeded for 240 minutes. The autoclave was then brought to room temperature by cooling with cold water, depressurized and opened for product analysis. The product analysis is shown in Table I.

EXAMPLE 2

13.5 grams of acrylonitrile, 0.31 grams of NNNN-tetramethylethylenediamine and 100 milliliters of methanol were placed in the glasslined autoclave. Next, 1.37 grams of $Co_2(CO)_8$ were added and the autoclave sealed.

The autoclave was charged with synthesis gas containing 5% $H_2$ to a pressure of 800 psi. The temperature was set at 95° C. and the reaction proceeded for 150 minutes. The autoclave was then brought to room temperature by cooling with cold water, depressurized and opened for product analysis. The product analysis is shown in Table I.

EXAMPLES 3 THRU 17

The procedure outlined in Example 1 was followed with only the ligand, molar ratio of cobalt carbonyl/ligand, temperature and pressure being varied. These variables are specified in Table I for each example. Table I also shows the product analysis for Examples 3 thru 17.

EXAMPLE 18

13.5 grams of acrylonitrile, 0.70 grams of NNNN-tetramethylbutanediamine, 100 milliliters of benzene and 9.78 grams of methanol were placed into a glasslined autoclave. Next, 1.37 grams of $Co_2(CO)_8$ were added and the autoclave sealed.

The autoclave was charged with synthesis gas containing 5% $H_2$ to a pressure of 800 psi. The temperature was set at 97.5° C. and the reaction proceeded for 90 minutes. The glasslined autoclave was then brought to room temperature by cooling with cold water, depressurized and opened for product analysis. The product analysis is shown in Table I.

EXAMPLES 19 thru 21

These examples followed the same procedure outlined in Examples 3 thru 17. The results are shown in Table I.

EXAMPLE 22

The procedure outlined in Example 18 was followed except that 100 milliliters of iso-octane was used instead of 100 milliliters of benzene and the reaction proceeded for 120 minutes rather than 90 minutes. The results are shown in Table I.

EXAMPLES 23 thru 29

The procedure outlined in Examples 3 thru 17 was followed in these examples. The results are shown in Table I.

EXAMPLES 30 thru 36

The procedure outlined in Example 18 was followed except that the solvent, ligand, carbonyl/ligand molar ratio, and reaction time were varied. The specific values for these variables are shown in Table I for each example. The product analysis for Examples 30 thru 36 is also shown in Table 1.

EXAMPLE 37

In each of the above examples, methanol, was used as the compound containing a replaceable hydrogen atom. In Examples 37 and 38, other alcohols were used. In Example 37, the alcohol reactant was ethanol.

TABLE I

CARBONYLATION WITH POLYAMINE LIGANDS

Catalyst: $Co_2(CO)_8$ + Ligand
Unsaturated Olefin Feed: Acrylonitrile
Autoclave Charged with Synthesis Gas (5% $H_2$)

| Example | Ligand | $Co_2(CO)_8$/Ligand (Mole %) | Solvent | Temp (°C.) | Pres (psi) | Time (Min) | Conv (%) |
|---|---|---|---|---|---|---|---|
| 1 | EDA | 1:1 | MeOH | 100 | 800 | 240 | 92.00 |
| 2 | TMED | 1:.66 | MeOH | 95 | 800 | 150 | 100.00 |
| 3 | TMED | 1:1.3 | MeOH | 95 | 800 | 120 | 68.70 |
| 4 | TMPD | 1:.66 | MeOH | 95 | 800 | 90 | 95.70 |
| 5 | TMPD | 1:1.3 | MeOH | 95 | 800 | 180 | 72.40 |
| 6 | TMBD | 1:.66 | MeOH | 95 | 800 | 120 | 84.93 |
| 7 | TMBD | 1:1.3 | MeOH | 95 | 800 | 180 | 38.36 |
| 8 | TMHD | 1:.66 | MeOH | 95 | 800 | 180 | 60.47 |
| 9 | TMHD | 1:1.3 | MeOH | 95 | 800 | 180 | 24.10 |
| 10 | TMPhD | 1:.66 | MeOH | 95 | 800 | 60 | 88.90 |
| 11 | TMPD | 1:2 | MeOH | 95 | 800 | 180 | 10.24 |
| 12 | TMPD | 1:1.3 | MeOH | 125 | 800 | 180 | 84.30 |
| 13 | TMPD | 1:1.3 | MeOH | 97.5 | 1200 | 180 | |
| 14 | TMPD | 1:.66 | MeOH | 125 | 800 | 180 | 95.50 |
| 15 | TMPD | 1:1.3 | MeOH | 97.5 | 1000 | 180 | 100.00 |
| 16 | TMPD | 1:.66 | MeOH | 97.5 | 800 | 180 | 34.50 |
| 17 | TMPD | 1:1.3 | MeOH | 97.5 | 600 | 180 | 27.60 |
| 18 | TMBD | 1:.60 | Benzene + MeOH | 97.5 | 800 | 90 | 100.00 |
| 19 | PvPyrl | 1:1 | MeOH | 97.5 | 800 | 180 | 63.20 |
| 20 | TMBD | 1:.66 | MeOH | 97.5 | 800 | 180 | 87.70 |
| 21 | TMPD | 1:.66 | MeOH | 75 | 800 | 180 | 90.20 |
| 22 | TMBD | 1:.60 | Isoctane + MeOH | 97.5 | 800 | 120 | 95.60 |
| 23 | TMPD | 1:.66 | MeOH | 97.5 | 800 | 180 | 67.70 |
| 24 | TMPD | 1:.66 | MeOH | 97.5 | 800[1] | 180 | 95.70 |
| 25 | TMPD | 1:.66 | MeOH | 97.5 | 800[2] | 180 | 10.60 |
| 26 | DIABLO | 1:2 | MeOH | 97.5 | 800 | 180 | 33.70 |
| 27 | TAD | 1:0.5 | MeOH | 97.5 | 800 | 180 | 78.70 |
| 28 | TEEDA | 1:1.0 | MeOH | 97.5 | 800 | 180 | 70.80 |
| 29 | TMPD | 1:.66 | MeOH | 97.5 | 800 | 180 | 51.80 |
| 30 | Pyridazine | 1:1:2 | DMP + MeOH | 97.5 | 800 | 50 | 49.70 |
| 31 | Pyridazine | 1:1:2 | DMP + MeOH | 97.5 | 800 | 120 | 78.60 |
| 32 | Pyridazine | 1:1:2 | DMP + MeOH | 97.5 | 800 | 135 | 27.40 |
| 33 | Pyrimidine | 1:1 | DMP + MeOH | 97.5 | 800 | 60 | 50.90 |
| 34 | Pyrimidine | 1:1 | DMP + MeOH | 97.5 | 800 | 150 | 60.80 |
| 35 | Pyrazine | 1:1 | DMP + MeOH | 97.5 | 800 | 60 | 20.10 |
| 36 | Pyrazine | 1:1 | DMP + MeOH | 97.5 | 800 | 150 | 75.50 |

Yields (%)

TABLE I-continued

| Example | 3-CE | 2-CE | PN | 3-CPA | 3-CPAA | 3-MPN | Other |
|---|---|---|---|---|---|---|---|
| 1 | 21.60 | 31.50 | 6.60 | 21.60 | 30.70 | 0.40 | 7.70 |
| 2 | 10.69 | 46.55 | 11.38 | — | 14.83 | 2.41 | 14.14 |
| 3 | 9.89 | 62.80 | 2.98 | — | 2.09 | 0.57 | 21.67 |
| 4 | 0.53 | 90.90 | 2.70 | — | 4.35 | 0.13 | 1.38 |
| 5 | 2.21 | 91.33 | 2.73 | — | — | 0.52 | 3.20 |
| 6 | 11.50 | 81.89 | 1.85 | — | 4.40 | 0.22 | 0.17 |
| 7 | — | 87.80 | — | — | — | 6.50 | 5.75 |
| 8 | 9.64 | 81.30 | 4.28 | — | 2.06 | 2.31 | 0.41 |
| 9 | — | — | — | — | — | 89.32 | 10.68 |
| 10 | 11.20 | 79.50 | 3.04 | — | 5.54 | 0.20 | 0.49 |
| 11 | — | — | — | — | — | 74.10 | 25.90 |
| 12 | 0.13 | 93.90 | 2.79 | — | 1.08 | 1.22 | 0.90 |
| 13 | 0.18 | 91.83 | — | 1.62 | — | 5.08 | — |
| 14 | 0.55 | 87.40 | 4.06 | — | 6.48 | 0.21 | 5.94 |
| 15 | 3.60 | 31.60 | 6.40 | — | 54.00 | 0.80 | 3.70 |
| 16 | — | — | — | — | 5.72 | 91.80 | 2.50 |
| 17 | — | — | — | — | — | 100.00 | — |
| 18 | 10.90 | 78.70 | 9.59 | — | — | 0.41 | 0.44 |
| 19 | 4.37 | 55.40 | 11.60 | 5.61 | 11.60 | 7.77 | 3.71 |
| 20 | 0.55 | 92.90 | 1.49 | 0.93 | 2.41 | 0.23 | 1.46 |
| 21 | 9.87 | 84.53 | 1.61 | — | 2.82 | 1.07 | 0.10 |
| 22 | 2.00 | 90.80 | — | — | — | — | — |
| 23 | 0.55 | 94.30 | 3.68 | — | — | 0.91 | 0.61 |
| 24 | 0.38 | 93.10 | 1.91 | 0.89 | 2.98 | 0.77 | 0.15 |
| 25 | — | — | — | — | — | 91.40 | 8.60 |
| 26 | — | 64.20 | — | — | — | 15.00 | 20.80 |
| 27 | 7.42 | 24.90 | 31.30 | — | 17.30 | 15.60 | 3.40 |
| 28 | 5.50 | 43.30 | 17.60 | 5.70 | 12.90 | 9.30 | 5.60 |
| 29 | 24.00 | 66.50 | — | — | 1.00 | 4.60 | 3.80 |
| 30 | 8.90 | Trace | — | 78.40 | 12.60 | — | — |
| 31 | 8.30 | 7.70 | 6.20 | 55.90 | 21.90 | — | — |
| 32 | 20.50 | 19.70 | — | 49.50 | 9.30 | 1.00 | — |
| 33 | 5.60 | Trace | — | 68.70 | 10.60 | 15.10 | — |
| 34 | Trace | 20.00 | 9.20 | 57.60 | 12.40 | 0.80 | — |
| 35 | 3.20 | — | — | 90.40 | 6.40 | — | — |
| 36 | 2.90 | 4.90 | 4.10 | 70.20 | 17.90 | — | — |

[1]Synthesis gas contained 2.2% $H_2$
[2]Syntheisi gas contained 0.0% $H_2$

COMPOUND NAME ABBREVIATIONS

| Abbreviation | Compound Name |
|---|---|
| 2 CE | methyl-α-cyanopropionate |
| 3 CE | methyl-β-cyanopropionate |
| 3 CPA | 3-cyano-propionaldehyde |
| 3 CPAA | 3-cyano-propionaldehyde dimethyl acetal |
| DIABLO | diazabicyclo (2.2.2) octane |
| DMP | dimethylphthalate |
| EDA | ethylenediamine |
| 3-MPN | 3-methoxy propionitrile |
| PN | propionitrile |
| PVPYRL | polyvinylpyrrolidone |
| TAD | tetraazadecane |
| TEEDA | tetraethylethylenediamine |
| TMED | NNNN-tetramethylethylenediamine |
| TMBD | NNNN-tetramethylbutanediamine |
| TMHD | NNNN-tetramethyl-1,6-hexanediamine |
| TMPD | NNNN-tetramethyl-1,3-propanediamine |
| TMPhD | NNNN-tetramethylphenylenediamine |

EXAMPLE 37

13.5 grams of acrylonitrile, 0.18 grams of NNN'N'-tetramethylpropanediamine and 100 milliliters of ethanol were placed into a glasslined autoclave. Next, 0.69 grams of $Co_2(CO)_8$ were added and the autoclave sealed.

The autoclave was charged with synthesis gas containing 5% $H_2$ to a pressure of 800 psi. The temperature was set at 97.5° C. and the reaction proceeded for 180 minutes. The conversion was 90.3% and the results are shown below:

| Product | Yield (%) |
|---|---|
| ethyl-2-cyanopropionate | 89.9 |
| ethyl-3-cyanopropionate | 4.8 |
| Propionitrile | 1.1 |

EXAMPLE 38

In Example 38 butanol was used as the alcohol reactant. 13.5 grams of acrylonitrile, 0.70 grams of NNN'N'-tetramethylpropanediamine and 100 milliliters of butanol were placed into a glasslined autoclave. Next, 1.37 grams of $Co_2(CO)_8$ were added and the autoclave sealed. The autoclave was charged with synthesis gas containing 5% H₂ to a pressure of 200 psi. The temperature was set at 97.5° C. and the reaction proceeded for 180 minutes. The glasslined autoclave was brought to room temperature by cooling with cold water, depressurizing and opening for product analysis. The conversion was 100% and the results are shown below:

| Product | Yield (%) |
|---|---|
| t-butyl-2-cyanopropionate | 93.6 |
| propionitrile | 4.08 |
| 3-cyano-propionaldehyde dimethyl acetal | 1.89 |

EXAMPLE 39

Examples 39 thru 42 were conducted using an olefinically unsaturated compound other than acrylonitrile. In Example 39, the olefinically unsaturated compound is propylene.

6.84 grams of propylene, 0.34 grams of NNN'N'-tetramethylpropanediamine, 100 milliliters of dimethylphthalate and 9.78 grams of methanol were placed into a glasslined autoclave. Next, 1.37 grams of cobalt carbonyl were added and the autoclave sealed. The autoclave was charged with synthesis gas containing 5% H₂ to a pressure of 800 psi. The temperature was set at 97.5° C. and the reaction proceeded for 330 minutes. The glasslined autoclave was then brought to room temperature by cooling with cold water, depressurized and opened for product analysis. The results are shown below:

| Product | Yield (%) |
|---|---|
| isobutylaldehyde | 15.5 |
| butylaldehyde | 20.1 |
| methylisobutyrate | 13.0 |
| methylbutyrate | 51.4 |

EXAMPLE 40

The olefinically unsaturated compound used in Example 40 was methylacrylate. 6.75 grams of methylacrylate, 0.35 grams of NNN'N'-tetramethylpropanediamine and 100 milliliters of methanol were placed into a glasslined autoclave. Next, 0.70 grams of cobalt carbonyl were added and the autoclave sealed. The autoclave was charged with synthesis gas containing 5% H₂ to a pressure of 800 psi. The temperature was set at 97.5° C. and the reaction proceeded for 210 minutes. The glasslined autoclave was then brought to room temperature by cooling with cold water, depressurized and opened for product analysis. Dimethylsuccinate was obtained in a 30% yield.

EXAMPLE 41

The olefinically unsaturated compound in Example 41 was allyl alcohol. 7.4 grams of allyl alcohol, 0.18 grams of NNN'N'-tetramethylpropanediamine and 100 milliliters of methanol were placed into a glasslined autoclave. Next, 0.69 grams of cobalt carbonyl were added and the autoclave sealed.

The autoclave was charged with synthesis gas containing 5% H₂ to a pressure of 800 psi. The temperature was set at 97.5° C. and the reaction proceeded for 180 minutes. The glasslined autoclave was brought to room temperature by cooling with cold water, depressurized and opened for product analysis. A 50% yield of butyrolactone was obtained.

EXAMPLE 42

The olefinically unsaturated compound used in Example 42 was 3-pentenenitrile. 3.0 grams of 3-pentenenitrile, 0.17 grams of NNN'N'-tetramethylpropanediamine and 100 milliliters of methanol were placed into a glasslined autoclave. Next, 0.76 grams of Co₄(CO)₁₂ were added and the autoclave sealed.

The autoclave was charged with synthesis gas containing 5% H₂ to a pressure of 800 psi. The temperature was set at 125° C. and the reaction proceeded for 180 minutes. Methyl-5-cyanovalorate was obtained in a 13.25% yield.

EXAMPLE 43

In the following example, the compound containing a replaceable hydrogen atom was hydrogen gas.

13.5 grams of acrylonitrile, 0.34 grams of NNN'N'-tetramethylpropanediamine and 100 milliliters of benzene were placed into a glasslined autoclave. Next, 1.37 grams of cobalt carbonyl were added and the autoclave sealed.

The autoclave was charged with synthesis gas containing 50% H₂ to a pressure of 800 psi. The temperature was set at 75° C. and the reaction proceeded for about 120 minutes. The glasslined autoclave was then brought to room temperature by cooling with cold water, depressurized and opened for product analysis. The conversion was 99.7% and the results are shown below:

| Product | Yield (%) |
|---|---|
| Beta-cyano-propionaldehyde | 98.3 |
| Propionitrile | 1.7 |

COMPARATIVE EXAMPLE A

Experiments were conducted comparing the selectivity of a monoamine ligand to a diamine ligand at the same concentration level. The monoamine experimental method is shown below.

0.385 grams of NN-dimethylethylamine (monoamine), 13.5 grams of acrylonitrile and 100 grams of methanol were placed into a glasslined autoclave. Next, 1.37 grams of cobalt carbonyl was added and the autoclave sealed.

The autoclave was charged with synthesis gas containing 5% H₂ to a pressure of 800 psi. The temperature was set at 97.5° C. and the reaction proceeded for 130 minutes. The glasslined autoclave was then brought to room temperature by cooling with cold water, depressurized and opened for product analysis. The results are shown in Table II.

EXAMPLE 44

The diamine experimental method consisted of placing 0.385 grams of NNN'N'-tetramethylbutanediamine (diamine), 13.5 grams of acrylonitrile and 80 grams of methanol into a glasslined autoclave. Next, 1.37 grams of cobalt carbonyl were added and the autoclave sealed.

The autoclave was charged with synthesis gas containing 5% H₂ to a pressure of 800 psi. The temperature was set at 97.5° C. and the reaction proceeded for 130 minutes. The glasslined autoclave was brought to room temperature by cooling with cold water, depressurized and opened for product analysis. The results are shown in Table II.

TABLE II
COMPARISON OF MONOAMINE AND DIAMINE LIGAND

Catalyst: $Co_2(CO)_8$ + Ligand
Unsaturated Olefin Feed: Acrylonitrile
Autoclave Charged with Synthesis Gas (5% $H_2$)

| Example | Ligand | $Co_2(CO)_8$/Ligand (Mole %) | Solvent | Temp (°C.) | Pres (psi) | Time (Min) | Conv (%) | Yields (%) 3-CE | 2-CE | PN | 3-CPA | 3-CPAA | 3-MPN | Other |
|---|---|---|---|---|---|---|---|---|---|---|---|---|---|---|
| A (monoamine) | NN ethyl dimethyl amine | 1:0.66 | MeOH | 97.5 | 800 | 130 | 89.90 | 1.60 | 45.80 | | | 27.30 | | |
| 44 (diamine) | NNNN tetramethyl butanediamine | 1:0.66 | MeOH | 97.5 | 800 | 130 | 84.90 | 11.50 | 81.90 | | | 4.40 | | |

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

We claim:

1. A process for the production of predominantly branched chain esters and amides in the liquid phase comprising contacting acrylonitrile with carbon monoxide and a compound containing a replaceable hydrogen atom represented by the formula H—Y
wherein Y is selected from the group consisting of:
(1) $OR_5$ wherein $R_5$ is a $C_{1-30}$ alkyl; and
(2)

wherein $R_6$ and $R_7$ are each independently selected from $C_{1-10}$ alkyls;
in the presence of $H_2$ in an amount less than 10% by volume of total $H_2$ and carbon monoxide present, and in the presence of a catalyst comprising a polyamine promoter ligand and at least one of cobalt carbonyl and ruthenium carbonyl, said polyamine promoter ligand being selected from the group consisting of alkyl-substituted and unsubstituted alkylenediamines, methyl-substituted and unsubstituted phenylenediamines, diazobicyclo (2.2.2) octane and polyvinylpyrrolidone, and wherein the process is conducted at a temperature of about 50° C. to 150° C. and a pressure of between about 100 and 2500 psi, and wherein the molar ratio of HY to said olefinically unsaturated compound is about 0.5–100:1.

2. A process as in claim 1 wherein a branched chain ester is produced and wherein Y is selected from the group consisting of $OR_5$ wherein $R_5$ is a $C_{1-10}$ alkyl.

3. The process of claim 1 wherein Y is selected from the group consisting of:
(1) $OR_5$ wherein $R_5$ is a $C_{1-10}$ alkyl;
(2)

wherein $R_6$ and $R_7$ are each independently selected from $C_{1-4}$ alkyls.

4. The process of claim 3 wherein the compound containing a replaceable hydrogen atom is selected from the group consisting of methanol, ethanol, propanol and butanol.

5. The process of claim 4 wherein the compound containing a replaceable hydrogen atom is methanol.

6. The process of claim 1 wherein the $H_2$ comprises 0.5% to 7.5% by volume of the total amount of carbon monoxide and $H_2$ in the reaction system.

7. The process of claim 1 wherein the process is conducted in the presence of an organic solvent.

8. The process of claim 7 wherein the solvent is selected from the group consisting of an alcohol, aromatic, ester, nitrile and dinitrile.

9. The process of claim 8 wherein the solvent is an alcohol or ester.

10. The process of claim 1 wherein the temperature is about 100° C.

11. The process of claim 1 wherein the pressure is between 700 and 1,000 psi.

12. The process of claim 1 wherein said molar ratio is 1-10:1.

* * * * *